US00PP17862P2

(12) United States Plant Patent
Wain

(10) Patent No.: US PP17,862 P2
(45) Date of Patent: Jul. 10, 2007

(54) ***CHRYSANTHEMUM* PLANT NAMED 'YOKILLEEN'**

(50) Latin Name: *Chrysanthemum×morifolium*
Varietal Denomination: Yokilleen

(75) Inventor: Peter Wain, Southampton (GB)

(73) Assignee: Yoder Brothers Inc., Barberton, OH (US)

( * ) Notice: Subject to any disclaimer, the term of this patent is extended or adjusted under 35 U.S.C. 154(b) by 8 days.

(21) Appl. No.: 11/269,176

(22) Filed: Nov. 8, 2005

(51) Int. Cl.
*A01H 5/00* (2006.01)

(52) U.S. Cl. ..... Plt./287

(58) Field of Classification Search ..... Plt./287
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Chrysanthemum* plant named 'Yokilleen', characterized by its upright, outwardly spreading and mounded plant habit; strong and freely branching growth habit; dark green-colored foliage; uniform flowering response and habit; early and freely flowering habit; decorative-type inflorescences with quilled-shaped and bright green-colored ray florets; and good postproduction longevity with plants maintaining good substance and color for about three weeks in an interior environment.

2 Drawing Sheets

Botanical designation: *Chrysanthemum×morifolium.*
Cultivar denomination: 'Yokilleen'.

BACKGROUND OF THE INVENTION

The present Invention relates to a new and distinct cultivar of *Chrysanthemum* plant, botanically known as *Chrysanthemum×morifolium* and hereinafter referred to by the name 'Yokilleen'.

The new *Chrysanthemum* is a product of a planned breeding program conducted by the Inventor in Fareham, Hampshire, United Kingdom. The objective of the program is to create or discover new potted *Chrysanthemum* cultivars that are suitable for year-round production with uniform plant growth habit, good vigor and strong branching habit, numerous inflorescences, desirable inflorescences form and floret colors, fast and uniform flowering response and good postproduction longevity.

The new *Chrysanthemum* originated from a cross-pollination made in February, 2000 in Fareham, Hampshire, United Kingdom, of a proprietary selection of *Chrysanthemum×morifolium* identified as code number P283D 6, not patented, as the female, or seed, parent with a proprietary selection of *Chrysanthemum×morifolium* identified as code number P363D 1, not patented, as the male, or pollen, parent. The new *Chrysanthemum* was discovered and selected by the Inventor as a single flowering plant within the progeny of the stated cross-pollination grown in a controlled environment in Fareham, Hampshire, United Kingdom in 2001. The selection of this plant was based on its uniform plant growth habit, good vigor and strong branching habit, desirable inflorescence form and floret colors, fast and uniform flowering response, and good postproduction longevity.

Asexual reproduction of the new *Chrysanthemum* by vegetative tip cuttings was first conducted in Fareham, Hampshire, United Kingdom in 2001. Asexual reproduction by cuttings has shown that the unique features of this new

*Chrysanthemum* are stable and reproduced true to type in successive generations.

SUMMARY OF THE INVENTION

The cultivar Yokilleen has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yokilleen'. These characteristics in combination distinguish 'Yokilleen' as a new and distinct *Chrysanthemum:*

1. Upright, outwardly spreading and mounded plant habit.
2. Strong and freely branching growth habit.
3. Dark green-colored foliage.
4. Uniform flowering response and habit.
5. Typically grown as a spray-type.
6. Early and freely flowering habit.
7. Decorative-type inflorescences with quilled-shaped ray florets.
8. Bright green-colored ray florets.
9. Good postproduction longevity with plants maintaining good substance and color for about three weeks in an interior environment.

Plants of the new *Chrysanthemum* can be compared to plants of the female parent selection. Plants of the new *Chrysanthemum* differ from plants of the female parent selection in the following characteristics:

1. Plants of the new *Chrysanthemum* flower earlier than plants of the female parent selection.
2. Plants of the new *Chrysanthemum* and the female parent selection differ in ray floret coloration as plants of the female parent selection have yellow green-colored ray florets.

Plants of the new *Chrysanthemum* can be compared to plants of the male parent selection. Plants of the new *Chrysanthemum* differ from plants of the male parent selection in the following characteristics:

1. Plants of the new *Chrysanthemum* are taller than plants of the male parent selection.
2. Plants of the new *Chrysanthemum* have larger inflorescences than plants of the male parent selection.
3. Plants of the new *Chrysanthemum* flower earlier than plants of the male parent selection.

Plants of the new *Chrysanthemum* can be compared to plants of the cultivar Revert, not patented. In side-by-side comparisons conducted in Alva, Fla., plants of the new *Chrysanthemum* differed from plants of the cultivar Revert in the following characteristics:

1. Plants of the new *Chrysanthemum* were more compact than plants of the cultivar Revert.
2. Plants of the new *Chrysanthemum* were more outwardly spreading than plants of the cultivar Revert.
3. Plants of the new *Chrysanthemum* had smaller inflorescences than plants of the cultivar Revert.
4. Plants of the new *Chrysanthemum* flowered about one week earlier than plants of the cultivar Revert.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum.*

The photograph on the first sheet comprises a side perspective view of typical flowering plants of 'Yokilleen' grown as spray-types.

The photograph on the second sheet comprises a close-up view of typical inflorescences of 'Yokilleen' grown as spray-types.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the summer in Salinas, Calif., in a fiberglass-covered greenhouse and under conditions which approximate those generally used in commercial potted *Chrysanthemum* production. During the production of these plants, the following conditions were measured: day temperatures, 21° C. to 27° C.; night temperatures, 17° C. to 19° C.; and light levels, 5,000 to 6,000 foot-candles. Four unrooted cuttings were directly stuck in 15-cm containers, exposed to long day/short night conditions, and pinched once about two weeks later. About one week after the pinch, the photoinductive short day/long night treatments were initiated. Plants used for the description were grown as spray-types. Measurements and numerical values represent averages of typical flowering plants.

Botanical classification: *Chrysanthemum×morifolium* cultivar Yokilleen.

Commercial classification: Decorative-type potted *Chrysanthemum.*

Parentage:

*Female, or seed, parent.*—Proprietary selection of *Chrysanthemum×morifolium* identified as code number P283D 6, not patented.

*Male, or pollen, parent.*—Proprietary selection of *Chrysanthemum×morifolium* identified as code number P363D 1, not patented.

Propagation:

*Type.*—Terminal tip cuttings.

*Time to initiate roots.*—About four days at 21° C.

*Time to produce a rooted cutting.*—About ten days at 21° C.

*Root description.*—Fibrous; white, close to 155D, in color.

*Rooting habit.*—Freely branching; moderately dense.

Plant description:

*Appearance.*—Herbaceous decorative-type potted *Chrysanthemum* that is typically grown as a spray-type. Upright with lateral branches outwardly spreading; uniformly mounded crown. Strong and freely branching growth habit; about four lateral branches develop after removal of terminal apex (pinching); dense and full plants.

*Plant height.*—About 25 cm.

*Plant width.*—About 37 cm.

*Lateral branches.*—Length: About 18.5 cm. Diameter: About 6.5 mm. Internode length: About 1.4 cm. Strength: Strong. Texture: Pubescent. Color: 146A.

*Foliage description.*—Arrangement: Alternate; simple. Length: About 8.75 cm. Width: About 5.25 cm. Apex: Cuspidate. Base: Mostly attenuate. Margin: Palmately lobed, sinuses between lateral lobes mostly divergent. Texture, upper and lower surfaces: Pubescent. Color: Developing and fully expanded foliage, upper surface: Darker green than 147A. Developing and fully expanded foliage, lower surface: Close to 147B. Venation, upper surface: Close to 147A. Venation, lower surface: Close to 146A. Petiole length: About 2 cm. Petiole diameter: About 4 mm. Petiole texture, upper and lower surfaces: Pubescent. Petiole color, upper and lower surfaces: Close to 146A.

Inflorescence description:

*Appearance.*—Decorative-type inflorescence form with quilled-shaped ray florets. Inflorescences borne on terminals above foliage. Disk and ray florets develop acropetally on a capitulum. Inflorescences faintly fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Uniform and early flowering habit; plants exposed to three weeks of long day/short night conditions followed by photoinductive short day/long night conditions flower about seven weeks later.

*Postproduction longevity.*—Inflorescences maintain good color and substance for about three weeks in an interior environment.

*Quantity of inflorescences.*—About 18 inflorescences per lateral branch.

*Inflorescence bud.*—Height: About 7 mm. Diameter: About 8 mm. Shape: Oblate. Color: Close to 146A to more green than 147A.

*Inflorescence diameter.*—About 4 cm.

*Inflorescence height.*—About 1.7 cm.

*Diameter of disc.*—About 3 mm; inconspicuous.

*Receptacle diameter.*—About 5 mm.

*Receptacle height.*—About 6 mm.

*Ray florets.*—Length: About 1.9 cm. Width: About 3 mm. Corolla tube length: About 1.25 cm. Corolla tube diameter: About 1 mm. Shape: Quilled. Apex: Sharply acute. Base: Fused into a corolla tube. Margin: Entire. Orientation: Initially upright to eventually perpendicular. Texture, upper and lower surfaces: Smooth, glabrous; satiny. Number of ray florets per inflorescence: About 182 arranged in numerous whorls. Color: When opening, upper and lower surfaces: 144A to 145A. Fully opened, upper and lower surfaces: Close to 145A.

*Disc florets.*—Arrangement: Massed at center of receptacle. Length: About 6 mm. Diameter, apex: About 1.5 mm. Diameter, base: About 1 mm. Shape: Tubular; elongated. Apex: Five-pointed. Number of disc florets per inflorescence: About ten. Color: Immature: Close to 144A. Mature, apex: Close to 9A. Mature, mid-section: Close to 154D to 155D. Mature, base: Close to 155D.

*Phyllaries.*—Quantity per inflorescence: About 20 arranged in two to three whorls. Length: About 7 mm. Width: About 3 mm. Shape: Lanceolate. Apex: Acute. Base: Truncate. Margin: Entire. Texture, upper surface: Waxy, smooth. Texture, lower surface: Pubescent. Color, upper surface: Close to 146A. Color, lower surface: Close to 146A to more green than 147A.

*Peduncles.*—Length, terminal peduncle: About 1.5 cm. Length, fourth peduncle: About 2.1 cm. Diameter: About 2 mm. Angle: About 45° to 60° from vertical. Texture: Pubescent. Color: 146A.

*Reproductive organs.*—Androecium: Present on disc florets only. Anther length: About 2 mm. Anther color: Close to 9A. Pollen amount: None observed. Gynoecium: Present on both ray and disc florets. Style length: About 5 mm. Style color: Close to 154D. Stigma color: Close to 9A.

*Seed/fruit.*—Seed and fruit production has not been observed.

Disease/pest resistance: Resistance to pathogens and pests common to *Chrysanthemums* has not been observed on plants grown under commercial greenhouse conditions.

It is claimed:

1. A new and distinct cultivar of *Chrysanthemum* plant named 'Yokilleen', as illustrated and described.

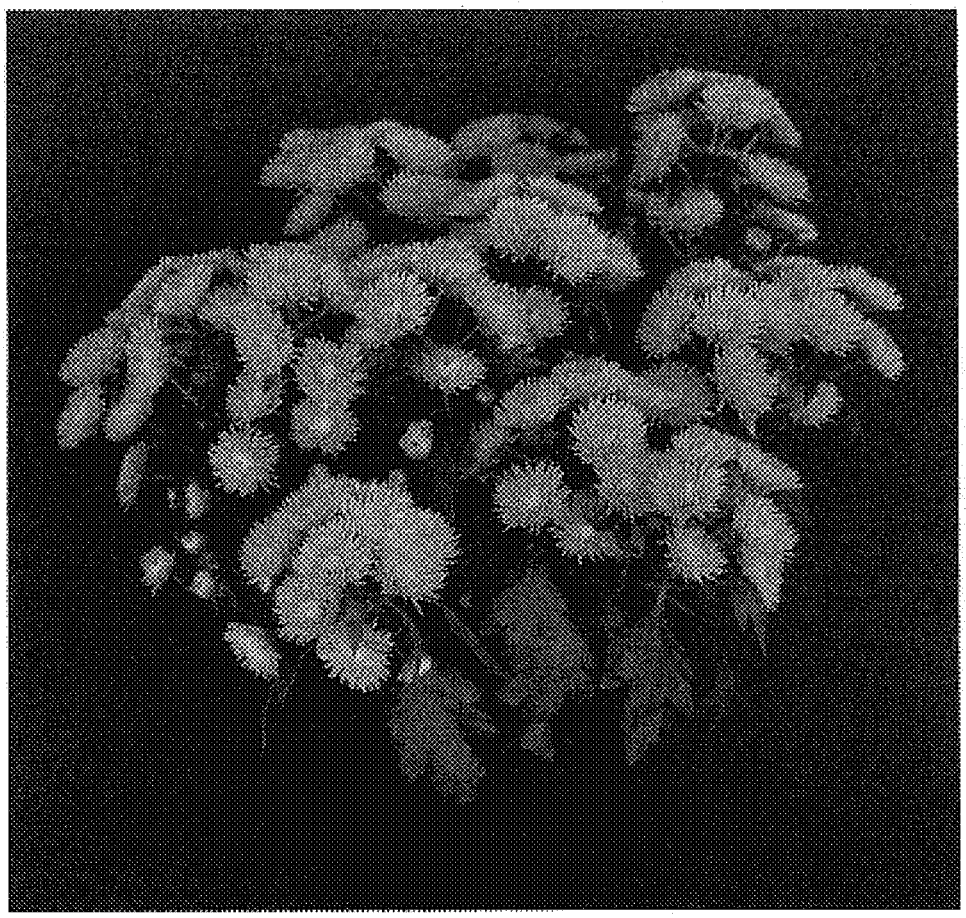

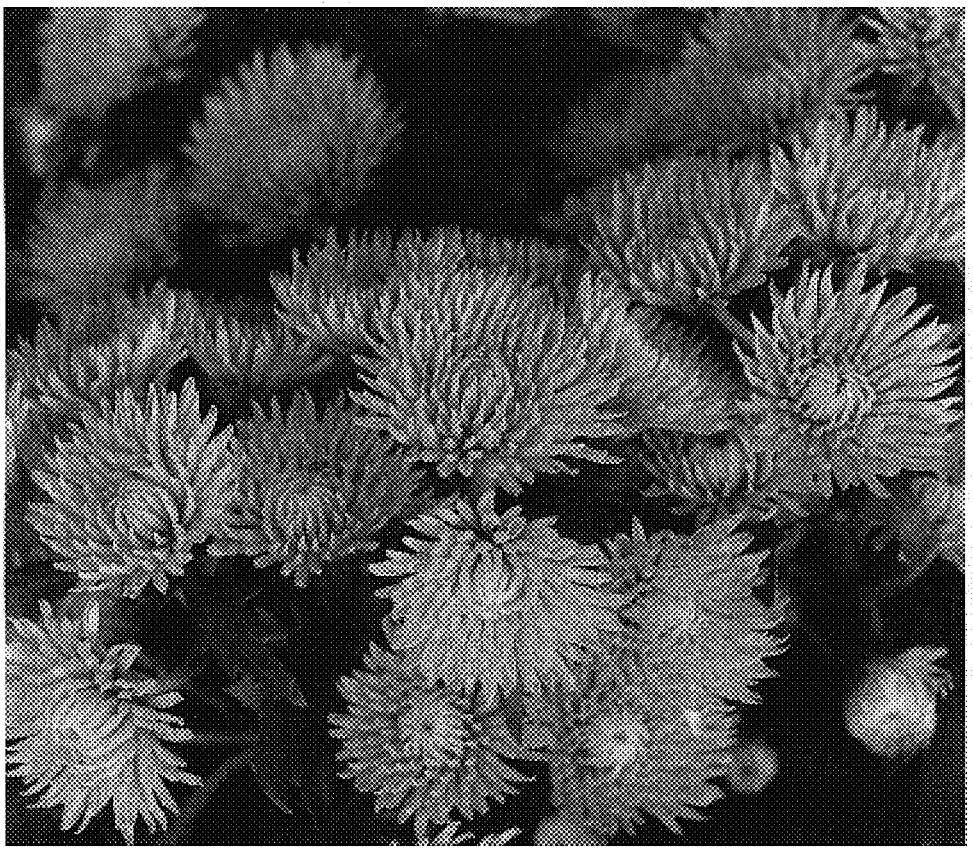

* * * * *